United States Patent [19]
Boussiba et al.

[11] Patent Number: 6,022,701
[45] Date of Patent: Feb. 8, 2000

[54] PROCEDURE FOR LARGE-SCALE PRODUCTION OF ASTAXANTHIN FROM HAEMATOCOCCUS

[75] Inventors: Sammy Boussiba, Omer; Avigad Vonshak, Midreshet Sede-Boker; Zvi Cohen, Omer; Amos Richmond, Midreshet Sede-Boker, all of Israel

[73] Assignee: Ben-Gurion University of the Negev Research and Development Authority, Beer-Sheva, Israel

[21] Appl. No.: 09/117,497

[22] PCT Filed: Jan. 30, 1997

[86] PCT No.: PCT/IL97/00042

§ 371 Date: Jul. 30, 1998

§ 102(e) Date: Jul. 30, 1998

[87] PCT Pub. No.: WO97/28274

PCT Pub. Date: Aug. 7, 1997

[30] Foreign Application Priority Data

Feb. 1, 1996 [IL] Israel ......................................... 116995

[51] Int. Cl.⁷ ...................................................... C12P 23/00
[52] U.S. Cl. ........................................... 435/67; 435/257.1
[58] Field of Search .................................... 435/67, 257.1

[56] References Cited

FOREIGN PATENT DOCUMENTS

WO 89/06910 8/1989 WIPO.

OTHER PUBLICATIONS

"Algal biotechnology products and processes—matching science and economics" Borowitzka, et al. Journal of Applied Phycology 4: 267–279, 1992.

"Critical Reviews in Biotechnology" Johnson, et al. Critical Reviews in Biotechnology, 11(297–326) (1991).

"Astaxanthin Production by a Green Alga, *Haematococcus plubialis* Accompanied with Morphological Changes in Acetate Media" Kobayashi, et al. Journal of Fermentation and Bioengineering, vol. 71, No.5, 335–339 (1991).

"A new tubular reactor for mass production of microalgae outdoors" Richmond, et al. Journal of Applied Phycology 5: 327–332, 1993.

"Antioxidant role of cartenoids in *Phaffia rhodozyma*" Schroeder, et al. Journal of General Microbiology 139, 907–912, 1993.

"A Vertical Alveolar Panel (VAP) for Outdoor Mass Cultivation of Microalgae and Cyanobacteria" Tredici, et al. Bioresource Technology 38, 153–159 (1991).

"Composition and presumed biosynthetic pathway of carotenoids in the astaxanthin—producing bacterium *Agrobacterium aurantiacum*" Yokohama, et al. FEMS Microbiology Letters 128, 139–144 (1995).

Derwent Computer Biotechds Abstract 92–03349 Boussiba et al "Astaxanthin accumulation in the green alga *Haematococcus pluvialis*; induction of pigment production" Plant Cell Physiol. (1991) 32, 7, 1077–82.

Derwent Computer Biotechds Abstract 94–13293 borowitzka "Large–scale algal culture systems; the next generation; alga e.g. *Phaeodactylum tricornutum* large–scale culture in a tubular photoreactor fermentor" Australas. Biotechnol.; (1994) 4, 4, pp. 212–215.

Derwent Computer Biotechds Abstract 89–06550 WO 8901977 (Mar. 9, 1989).

"Effect of temperature and irradiance on growth of *Haematococcus pluvialis* (Chlorophyceae)." Journal of Phycology, 30 (5). 1994 pp. 829–833 (Abstract) Biosis 95: 26587.

"Astaxanthin prepn. for medical antioxidant—by aerobic culture of *Haematococcus pluvialis* in the dark, then in light with carbon and active oxygen source to induce cyst formation." Database WPI, Section Ch, Week 9317. Derwent Publications Ltd. (Abstract)J05068585, Mar. 23, 1993.

"Enhancement and Determination of Astaxanthin Accumulation in Green Alga *Haematococcus pluvialis*. " Sammy Boussiba, et al. Methods in Enzymology. vol. 213. Carotenoids. pp. 386–391, 1992.

"Autotrophic growth and carotenoid prodution of *Haematococcus pluvialis* in a 30 liter air–lift photobioreactor." Mark Harker, et al. Chemical Abstracts, vol. 125, No. 17. XP002031369. (Oct. 21, 1996) CA(125):219715v.

"Astaxanthin accumulation in the green alga *Haematococcus pluvialis*." Sammy Boussiba, et al. Chemical Abstracts, vol. 115, No. 25. XP002031370. (Dec. 23, 1991)CA115: 275484z.

"Astaxanthin prodn.—comprises culturing green algae by temp. stress and induction of cyst formation in presence of active oxygen source and carbon source." Database WPI. Section Ch, Week 9516. Derwent Publications Ltd. (Abstract) J07039389(Feb. 10, 1995).

Primary Examiner—Herbert J. Lilling
Attorney, Agent, or Firm—Merchant & Gould PC

[57] ABSTRACT

A process for cultivating Haematococcus for the large scale production of astaxanthin-enriched Haematococcus cells comprises: (a) cultivating said Haematococcus cells under conditions suitable for optimal vegetative growth of said cells, wherein said conditions comprise growing the cells under a light intensity in the range of about 30–140 $\mu$mol photons.m$^{-2}$.S$^{-1}$ and at a temperature of between about 15–28° C.; and (b) collecting the cells grown according to (a) and cultivating them further under conditions suitable for optimal induction and accumulation of astaxanthin in said cells, wherein said conditions comprise inoculating said cells of (a) into a growth solution containing essentially a carbon source and growing said cells at a temperature of below 35° C.

17 Claims, 2 Drawing Sheets

PROCEDURE FOR LARGE-SCALE PRODUCTION OF ASTAXANTHIN FROM HAEMATOCOCCUS

FIELD OF THE INVENTION

The present invention concerns a process for cultivating Haematococ cells for the large-scale production of astaxanthin. The present invention also relates to a process for the large-scale production of astaxanthin-enriched Haematococcus cells.

BACKGROUND OF THE INVENTION AND PRIOR ART

Haematococcus is a group of green microalgae which are able to accumulate a large amount of a keto-carotenoid, astaxanthin, under certain environmental conditions (Boussiba et aL 1992). Astaxanthin is the major pigment imparting the red-pinkish color of salmon, trout and shrimp, whose prices are largely determined by their color. Currently, the major commercially available source of astaxanthin is in the form of a synthetic product, which is expensive (>US$ 3,000 per kilogram) and may contain astaxanthin compounds having an unnatural configuration. There is now a trend toward using natural sources of feed nutrients for the purpose of preparing feed for the above types of fish, and thus a less expensive and natural source of astaxanthin has been sought. This group of green microalgae appears to be the most promising source for this purpose. Although astaxanthin can be synthesized by other algae, bacteria and a few fungi (Schroeder & Johnson 1993; Yokoyama & Miki 1995), the amounts accumulated by Haematococcus (Boussiba & Vonshak 1991), however, surpass those obtained in the above noted sources. According to the present development of aquaculture, it is expected that by the year 2000, more than 100 tons of astaxanthin will be required (Johnson & An, 1991; Borowitzka, 1992). This potential demand could open a large market for microbially produced astaxanthin. Several reasearch groups have attempted to establish large production systems for Haematococcus.

However, no one has succeeded so far, due to the difficulties in enhancing astaxathin accumulation rate, preventing contamin ation by other microorganisms, and failure in special photobioreator design. An example of previous methods for producing astaxanthin and other pigments from Haematococcus is that described in the international patent application No. WO 89/06910.

*H. pluvialis* has a unique life cycle comprising two stages: a green, motile, vegetative stage in which the cells continuously divide and synthesize chlorophyll and a red, non-motile resting stage (cyst) in which cell division stops, chlorophyll content remains constant and astaxanthin content and cellular dry weight continuously increase. These two stages are illustrated in FIG. 1, which depicts graphically the relationship between four parameters of the growth of *H. pluvialis*, namely, chlorophyll, astaxanthin, dry weight and cell number. The optimal environ mental and nutritional conditions required for these two stages are quite different. For vegetative growth, full nutrient medium, moderate light intensity and adequate temperature and pH are essential. For the resting stage, however, no nutrient (except carbon) is required and higher light intensity (e.g., sunlight) is necessary for faster astaxanthin accumulation. Due to such discrepancies, the two stages must be separated into different cultivating systems with different medium accordingly. The growth strategies for each stage are also different. In the green stage, the optimal conditions for cell division are maintained to achieve the ma um cell number. In the red stage, the optimal inductive conditions must be provided for astaxathin accumulation. Heretofore, no such process has been developed for the effective large scale, two-stage or two-phase growth of Haematococcus cells, which answers the demands of each of the above growth stages of Haematococcus cells. The known processes suffer from a number of drawbacks, including the need for expensive growth media, apparatuses, use of sterile equipment and media and/or the use of expensive antibiotics or other anti-microbial agents to prevent contamination of the desired Haematococcus cultures by other microorganisms such as other microalgae, fungi, yeasts and bacteria. Thus, such processes are expensive and time-consuming to perform, and they also do not always provide a high yield of Haematococcus cells and/or of astaxanthin in the cultivated cells.

It is therefore one aim of the invention to provide a new two-phase cultivating procedure which allows for the production of vegetative green Haematococcus cells under controlled conditions of temperature, light intensity and nutrients and for the induction and production of red Haematococcus cells rich in astaxnthin under less stringently controlled conditions, of temperature and light, but under conditions of nutrient stress which accelerates the induction and accumulation of astaxanthin in the cells.

Likewise, it is another aim of the present invention to provide a process for the large-scale production of astaxanthin-enriched Haematococcus cells by utilization of the above-mentioned two-phase cultivating procedure.

Other aims of the present invention will be readily apparent from the following disclosure of the invention.

SUMMARY OF THE INVENTION

A new two-phase cultivating process for the large growth of Haematococcus cells for the purposes of large-scale astaxantin production has been developed. Likewise, in accordance with the present invention, a new process for the large-scale production of astaxanthin-enriched Haematococcus cells has been developed which utiizes the aforesaid two-phase cultivating process for cultivating Haematococcus cells.

In the two-phase cultivation process of the present invention, the first phase provides for the maintenance of optimal vegetative growth of the cells under controlled environmental conditions. This first stage or phase is characterized by the cells having continuous cell division, and astaxanthin/chlorophyll ratio between about 0.1 to 0.4 and an increase in chlorophyll content during the cultivation process, this being indicative of optimal Haematococcus cell growth. The results obtained in accordance with the present invention indicate that the production rate of cells grown under the conditions of this first phase was about 0.5 to 0.7 gr cells/l culture/day.

In the second phase of this procedure, astaxanthin induction and accumulation within the cells was achieved by collecting the cells from the above green cell culture and subjecting them to stress by nutrient deprivation by re-suspending the cells in tap water enriched with $CO_2$, followed by cultivation of the cells under exposure to full sunlight. It was found in accordance with the present invention that under these conditions of stress, encystment is rapid and that the cultivational duration usually lasts no longer than five to six days for the obtention of axtaxathin-enriched red cells. Further, in this second phase, the rate of biomass production was found to range between about 0.3 to 0.4 gr cells/l culture/day, and the amount of astaxanthin within the cells being about 3 to 5%, as determined from the dry biomass of cells collected and dried following the second phase of culture. It should be noted that heretofore no cultivation process has succeeded in providing Haematococcus cells in which the enrichedment of axtaxanthin is at such high levels, the previously known procedures having provided cells with up to about 2% astaxanthin.

Accordingly, the present invention provides:

A process for cultivating Haematococcus cells for the large scale production of axtazanthin-enriched Haematococcus cells comprising:

(a) cultivating said Haematococcus cells under conditions suitable for optimal vegetative growth of said cells, wherein said conditions comprise growing the cells under a light intensity in the range of about 30–140 $\mu$mol photons.m$^{-2}$s$^{-1}$ and at a emperature of between about 15–28° C.; and (b) collecting the cells grown according to (a) and cultivating them further under conditions suitable for optimal induction and accumulation of astaxanthin in said cells, wherein said conditions comprise inoculating said cells of (a) into a growth solution containing essentally a carbon source and growing said cells at a temperature of below 35° C.

One embodiment of the above process of the invention is the use of suitable photobioreactors for each stage of the cultivation process, such as for example, a vertical panel or a tubular photobioreactor.

Another embodiment of the above process of the invention is the cultivation of the cells in step (a) under conditions of light intensity in the range of about 70–90 $\mu$mol photons.m$^{-2}$s$^{-1}$ and at a temperature of between about 22–25° C.

Yet another embodiment of the above process of the invention is the cultivation of the cells in step (b) under conditions wherein the temperature is maintianed at below 32° C.

The present invention also provides a process for the large-scale production of astaxanthin-enriched Haematococcus cells comprising cultivating the Haematococcus cells according to steps (a) and (b) of the above process of the invention, and further comprising:

(c) harvesting the cells cultivated in (b) by collecting said cells, concentrating the collected cells, drying the concentrated cells and freezing the dried cells; and (d) processing the frozen dried cells of (c) by grinding them under cryogenic conditions in the presence of a suitable antioxidant to obtain an astaxanthin-enriched product.

Other aspects and embodiments of the present invention will be readily apparent from the following detailed description of the invention.

DETAILED DESCRIPTION OF PREFERRED EMBODIMENTS

Figure 1:
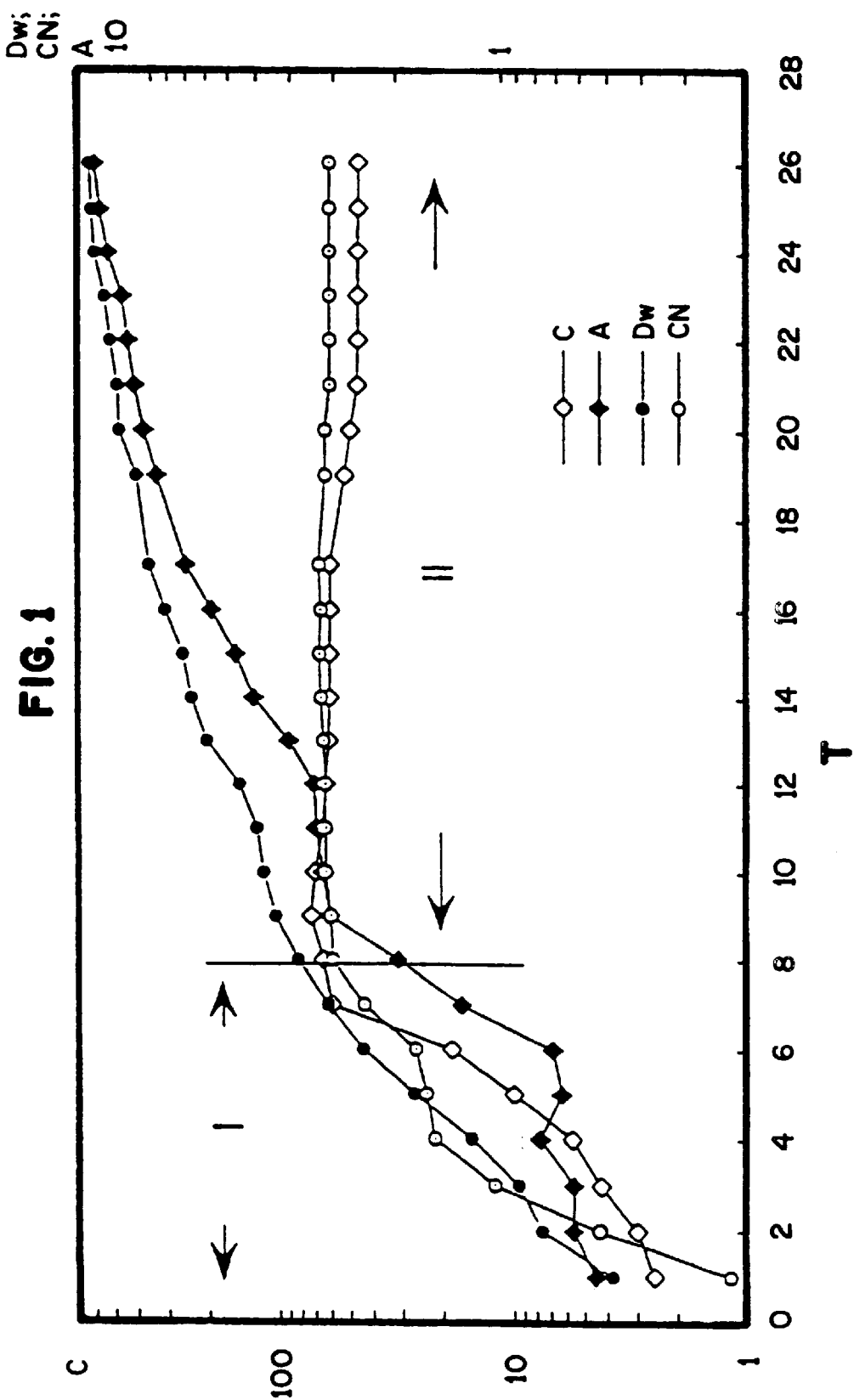
FIG. 1 depicts graphically the previously determined relationship between four parameters of growth of *Haematococcus pluvialis*: chlorophyll (open diamonds) astaxanthin (solid diamonds), dry weight of cells (solid circles), and cell number (open circles). These four parameters are depicted for the first, vegetative or "green" stage of cell growth and for the second "red" stage of growth in which astaxanthin accumulates. These four parameters are shown in the form of their relative amounts as a function of the duration of cell growth (time in days). In the Figure, "C-A" indicates the content of chlorophyll (open diamonds) or astaxanthin (solid diamonds), in mg·L$^{-1}$, "T" indicates the time (days), Dw is the dry weight (solid circles), "CN" is the cell number (X10$^{6}$·ml$^{-1}$) (open circles), "I" indicates the first stage, and "II" the second stage, of cell growth.

The present invention concerns processes for the cultivation of Haematococcus cells for large-scale production of astaxanthin-enriched Haematococcus cells; and for the large-scale production of astaxanthin-enriched cells employing such a cultivation process.

For the purposes of the processes of the invention, any of a number of strains of Haematococcus may be employed, for example, strains such as those shown in Table I below.

TABLE I

| Haematococcus Strains & Species | |
|---|---|
| Strains & Species | Source |
| *H. pluvialis* flotow | CCAG, Gottingen |
| *H. pluvialis* flotow | NIES Tsukuba, Japan |
| *H. lacustris* UTEX 16 | CCAT, USA |
| *H. pluvialis* flotow ETTL 1958/3 | Ceska republika |
| *H. pluvialis* Flo-TAKAOOVA 1983/1 | Same as above |
| *H. Droeabicensis* CCAP 43/2G | CCAP, UK |
| *H. pluvialis* Flo. 1844 em. Willie K-0084 | SCCAP, Denmark |

The above strains are well documented in the art. The preferred strain in accordance with the invention is the strain exemplified herein below, *H. pluvialis* Flo. (K-0084), which has amongst its characterics a very low tendency to clump, making it particularly useful for large-scale cultures.

It is to be understood that any other strain of Haematococcus which may be effectively subjected to the processes according to the invention would also be employable in accordance with the invention.

Many culture conditions and culture media are known for small-scale stock cultures and large-scale cultures of Haematococcus cells. However, for the purposes of the present invention, it has been found that the optimal culture conditions and media are actually the relatively simple culture conditions and media described herein below, these therefore being the preferred ones in accordance with the invention.

While many apparatuses, systems and conditions have been described for the growth of Haematococcus cells, none of these were able to address simply, efficiently and inexpensively the optimization of the two phases of Haematoccus cell growth. Accordingly, the preferred system, apparatus and conditions of the present invention are those exemplified herein below.

For the obtention of astaxanthin-enriched product from the induced "red" Haematococcus cells, many procedures have been described, for example, the procedures in WO 89/06910. While these procedures may be employed in accordance with the present invention, the preferred procedure is that of sedimentation in a funnel, of the collected red cells by virtue of their tendency to sediment, followed by centrifugation or filtration under vacuum to further concentrate the cells and drying of the concentrated cells. The dried cell mass is then preferably stored at very low temperatures (e.g., $-80°$ C. or even lower) under oxygen-free conditions, e.g., by vacuum packing, or preferably, by introduction into plastic bags or the like together with nitrogen ($N_2$) to remove the oxygen.

The final stage of producing an astaxanthin-enriched product in the form of small particles easily digested by fish may also be carried out in a number of ways as previously described in the art (for example, WO 89/06910). The preferred procedure is the one exemplified hereinbelow, which involves the use of a standard impact mill in which the dried cell mass is ground under cryogenic conditions in the presence of any suitable anti-oxidant to prevent oxidation of the astaxanthin-enriched product. This yields a powder-like product of small particle size particularly useful as an additive to fish meal, these small astaxanthin-rich particles being easily digested.

The present invention will now be described in the following non-limting example and the accompanying drawing.

The Cultivation Procedure for Cultivating Haematococcus Srains:

The procedure for cultivating the astaxanthin producing strins of Haematococcus in accordance with the present invention consists of two phases, Phase I and Phase II:

A. Phase I: Cultivation of Haematococcus Strains Under Controlled Environmental Conditions for Optimal Growth of Haematococcus Strains in Their So-called "green stage" of Growth.

A preferred Haematococcus strain, *Haematococcus pluvialis* Flo. (Strain No. K-0084) was obtained from the Scandinavia Culture Center for Algae and Protozoa, University of Copenhagen, Denmark, and was grown in a growth medium that was a Modified BG-11 medium containing:

(i) 0.32 g/l $K_2HPO_4.3H_2O$;

(ii) 0.2 g/l Mg $SO_4.7H_2O$; and (iii) 0.1 g/l $Na_2CO_3$, in addition to the other mineral constituents contained in the standard BG-11 growth medium (see, for example, Boussiba et al., 1992; Boussiba and Vonshak, 1991). The above addition of phosphate, magnesium and carbonate has been presently shown to provide optimal conditions for the green-stage growth of the cells. The non-modified BG-11 medium could not support long-term cultures or dense cultures due to its having less of these additives, such cultures in non-modified BG-11 often entering the red stage of growth (see also FIG. 1) earlier than desired, i.e., before the optimal amount of "green" cells has been obtaineid.

Basal medium was usually mixed with the Modified BG-11 medium for optimal growth of the Haematococcus strain in the initial stage only of groing the cells on ager plates or slants. The Basal Medium used was the Standard Basal Medium, as described by Kobayashi et al. (1991).

The Phase I growth procedure has the following steps:

(a) Cultivation of Haematococcus on solid agar slants or plates: An axenic strain (the above *H. pluvialis* strain) was grown and maintained in solid agar slants or plates containing a mixture of Modified BG-11 medium and Basal Medium (1:1 v/v) under conditions of light intensity ranging between 30 to 40 $\mu$mol photons.$m^{-2}.S^{-1}$ at 20° C. (see step (1), FIG. 2).

(b) Cultivation of liquid stock cultures of Haematococcus: Haematococcus cells from agar plates or slants of (a) above were inoculated into 100 ml of liquid medium (being the Modified BG-11 medium as in (a)) in 250 ml culture flasks and subsequently in larger flasks (or even glass columns) of between 500 ml—2.5 l in volume (see steps (2) and (3), FIG. 2). The flasks were incubated in a standard gyratory incubator having a controllable light source under conditions of light intensity ranging between 50 to 70 $\mu$mol photons.$m^{-2}.s^{-1}$ at 23° C. (or when glass columns were used, agitation was by way of aeration with an air mixture containing 1.5% $CO_2$ v/v). The cultures of Haematococcus obtained in these liquid stock cultures are cultures of the so-called "green culture" type, the Haematococcus cells being in the above-noted "green stage" of growth.

(c). Production of large-scale cultures of Haemctococcus in a photobioreactor: The green cultures from the liquid stock cultures (or inoccula) of (b) above were inoculated into a photobioreactor, in which the algae are agitated with a mixture of 1.5% $CO_2$ in air. This agitation also served to prevent clumping of the cells. It should be noted that the preferred strain *H. pluvialis* Flot. in fact has an extremely low tendency to clump, another advantage of this strain. The preferred photobioreactor used for these large-scale cultures was one of the vertical panel types of photobioreactors (see Tredici et al., 1991) having a very large surface area with respect to its volume for optimal large-scale production of Haematococcus cells in the "green stage" of growth (see step (4), FIG. 2). In this photobiareactor, the initial Haematococcus cell concentration was adjusted to between about 0.1 to 0.3×$10^6$ cells/ml, by dilution with fresh modified BG-11 medium. The light intensity was kept in the range of between 70–90 $\mu$mol photons.$m^{-2}.S^{-1}$ as provided by standard white cool fluorescent lamps having a 40 watt rating. The temperature in the photobioreactor was maintained in the range between 22–25° C. Under these culture conditions, it was possible to obtain a rate of Haematococcus cell production in the range between 0.5–0.7 g cells/l culture/day.

The procedure of the invention described above for the large-scale production of Haematococcus cells in their "green stage" of growth was found to be particularly advantageous for obtaining large amounts of cells, while at the same time preventing contamination of the large-scale culture by other microorganisms, for example, other algae, fungi, bacteria and the like; and this without the need for addition to the culture mediun of antibiotics or other antimicrobial agents to prevent such contamination. This advantage was achieved by the use of a relatively high initial Haemactococcus cell concentration which permitted the Haematococcus (*H. pluvialis*) cells to predominate immediately after their inoculation into the photobioreactor, thereby preventing any possible contnminating microorganisms to grow in the photobioreactor. This procedure is thus particularly eficient for growing large-scale cultures of Haematococcus, while effectively preventing contnmination by other microorganisms without the need for expensive and time-consuming steps such as careful sterilization of all apparatus and media, and use of antibiotics or any other anti-microbial agents.

B. Phase II: Cultivation of Haematococcus Strains Under Conditions for the Induction and Accumulation of Astaxanthin in the Haematococcus Cells—the So-called "red stage" of Haematocccus Cultivation.

Figure 2:
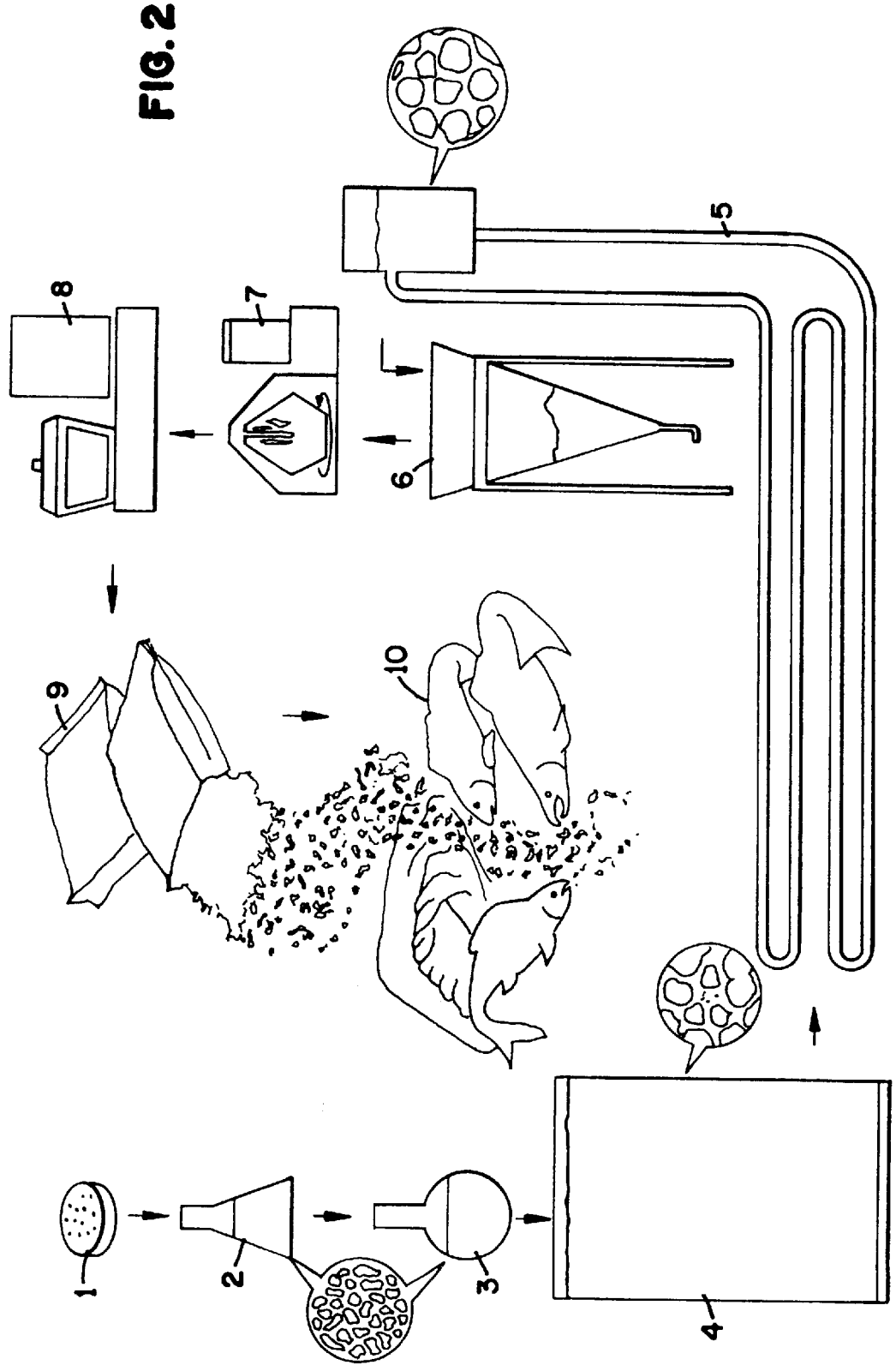
FIG. 2 is a schematic flow-chart of the processes of the invention wherein Haematococcus cells are prepared for large-scale cultivation by first growing them on agar plates or slants (1), followed by growth in successively large liquid cultures (2), (3) and inoculation of cultures from (3) into a photobioreactor of the vertical panel type (4) to facilitate large-scale vegetative or "green" cell growth under controlled conditions. The astaxanthin induction and accumulation is by inoculating cells from the photobioreactor (4) into another photobioreactor of the tubular photobioreactor type (5) under conditions of stress (nutrient depletion and higher light intensity) favorable for astaxanthin induction. The processing of the astaxanthin-enriched cells is provided by collection of cells from the photobioreactor of (5) and subjecting them to sedimentation in a funneel (6) followed by centrifugation (7) of the sedimented cells to provide a concentrated cell pellet which is ground under cryogenic conditions in an impact mill (8) to yield an astaxanthin-enriched product. The astaxanthin-enriched product from (8) can then be introduced as an ingredient for fish food (9) for various kinds of commercially important fish, for example, salmon, trout, shrimps, etc. (10). The above processes are described hereinbelow in detail in the exemplified embodiment of the invention.

As mentioned with respect to the Phase I cultivation procedure (A above), the Haematococcus strain of choice for this Phase II cultivation procedure was *Haematococcus pluvialis* Flo. (strain No. K-0084). The Phase II cultivation procedure was as follows:

a) The cultivation device used was a standard tubular photobioreactor (see step (5), FIG. 2, and see Richmond et al., 1993), which have volumes ranging from 100–1,000 liters, depending on the scale of production that is desired, and which contain as integral components commercially available PVC, acrylic (plexiglass) or polycarbonate tubes having a diameter of about 3.2 cm. In operation, the culture (Haematococcus cells in tap water, to which is added $CO_2$—see below) is circulated through the device using an air lift pump. It should be noted that for large-scale cultures or even small scale cultures, it is possible to use a standard diaphragm pump instead of the air lift pump.

b) For the cultivation of the Haematococcus cells in their "red stage" of growth, the green cells obtained from the Phase I cultivation procedure (A above) were used as inoccula for the above tubular photobioreactor. Optimally, the tubular photobioreactor was placed outdoors, this being in consideration of its size, as well as the fact that in the "red stage" of growth, the Haematococcus cells do not require the controlled light intensity which they require in their "green stage" of growth, hence sunlight isfavorable, and thereby this cultivation procedure also provides for a very economical way in which to produce the Haematococcus cells, and more particularly, to provide the stress conditions for the acceleration of astaxanthin induction and accumulation in these cells.

The green cells were inoculated in the form of a suspension of green cells in tap water, usually the green cells obtained from Phase I cultivation being re-suspended in tap water in an approximately 1:3 dilution. To the suspension of the green cells in the tubular photobioreactor, $CO_2$ was added (by injection into the tubes of the device). The temperature in the tubular photobioreactor was maintained at temperatures below 32° C.

It should be noted, however, that in a number of experiments it was found that the cells from the green-stage of growth could be collected, concentrated by natural sedimentation due to their tendency to sediment, and stored in a cold room (about 5° C.) for up to about 2–3 weeks, before their inoculation into the photobioreactor of the second stage (red-stage) of growth. Cells collected and stored in this way have thus also been depleted of their initial nutrient media, which serves also to induce stress in the cells and hence, astaxanthin production In fact, cells stored in this way and then introduced into the red-stage growth conditions showed a more rapid transition to the red stage and hence a more rapid induction and accumulation of astaxanthin.

The ability to stop the green-stage growth and collect the cells has another advantage, in that it also allows for a batch-wise production process, namely, it is not essential to go directly from green-stage to red-stage growth, an interval may be introduced as desired in consideration of production needs and limitations. This ability to stop the process between the green and red stages of growth has not been described prior to the present invention.

It was observed that under the above Phase II growth conditions, the rate of production of Haemtococcus cells was about 0.3–0.4 gr cells/l culture/day, and that the Haematococcus cells contained about 4% ast astaxanthin. Usually, the Phase II cuicivation procedure was performed for about five to six days before harvesting and drying of the cells which are rich in astaxanthin. The above amount of astaxanthin accumulated in the cells has not been achieved in any previously described large scale process.

As regards the above Phase II cultivation procedure, it was also observed that for outdoor cultures, especially those grown in the summer months when ambient temperatures can reach, in some places, as high as 40–45° C., temperature control is crucial. As noted above, for optimal cultivation of the Haematococcus cells, it is necessary to maintain the temperature in the tubular photobioreactor below 32° C., this having been achieved by use of a water spray, whereby cold water was sprayed directly onto the tubular photobioreactor to maintain its temperature below 32° C.

Further, in the "red stage" of growth, the Haematococcus cells require only carbon as the major nutrient source, this having been supplied, as noted above, by injection of $CO_2$ directly into the tubes of the tubular photobioreactor. This injection of $CO_2$ may be performed during the day and during the night. However, the $CO_2$ is essential only during the day, and thus a further saving of $CO_2$ may be achieved by stopping the injection during the night.

All of the above Phase II cultivation conditions, in particular, the requirement of the Haematococcus cells for only carbon as the major nutrient source and its supply in the form of $CO_2$, maintenance of cultivation temperatures below 32° C., and inoculation of relatively large amounts of cells at the outset (the green cells from the Phase I cultivation are in a high cell concentration and are only diluted about 1:3 before inoculation into the device for Phase II cultivation), all serve also to eliminate almost completely the possibility of contamination by other microorganisms such as, for example, other microalgae, of the Phase II cultures.

Thus, the above Phase II cultivation procedure of the invention provides a number of advantages over the previously described procedures:

(i) It is highly efficient for Haematococcus cell biomass increase, as well as for the induction and accumulation of astaxanthin in these cells: routinely, there was obtained about 0.3–0.4 gr cells/l culture/day of Haematococcus cells which contained about 4% ast a xthin per cell for such cultures which were usually grown for about five days.

(ii) It is very economical, as the basic device, the tubular photobioreactor, is relatively inexpensive, may be placed outdoors and does not require expensive maintenance or highly skiled personnel to operate. Further, the culture conditions are extremely inexpensive, the cells being grown in tap water (no distilled or sterilized water or growth media required), with the addition of essentially $CO_2$ as the major nutrient source.

(iii) It overcomes, without the need for any antibiotics or other anti-microbial agents, the major problem faced by this technology to date, that being the problem of contmination of the cultures by other microorganisms, such as, for example, other microalgae. The relatively simple culture conditions, in the Phase II procedure according to the invention, of high cell numbers inoculated initially, a minimal growth medium (tap water) having only a carbon source ($CO_2$), and temperature control (below 32° C.), and outdoor cultivation in a closed apparatus (the tubular photobioreactor), all serve to prevent the possibility of contaimation by other microorganisms.

As regards the various conditions of light intensity and temperature control, it should be noted that in a number of experiments directed at optimizing both of these parameters in the green and red stages of growth, it was observed that:

a) light intensity in the green phase could be anywhere in the range from 60–110 $\mu$mol photons.$m^{-2}s^{-1}$ and temperature could also be in the range between 18–28° C. The best results were obtained with the above noted naowed ranges of light intensity and temperature.

b) The upper limit for the temperature in the red stage/phase could in fact reach 35° C., while the lower limit in this stage could be as low as 2° C. The best results were obtained when the upper limit is maintained below 32° C. and the lower limit at 15° C.

Further, in both green and red stages, it was possible to use any of a number of photobioreactors, for example, for the green stage, the same type of reactor as used for the red stage may be employed so long as the optimal culture conditions are maintained; and for the red stage, a panel type reactor as used in the green stage has also been used to provide equally good results. Further, a tubular reactor in which algae were circulated by means of a pump has also been used with success.

C. Harvesting of Haematococcus Cells Following the "red stage" Cultivation Procedure (Phase II cultivation).

Following the Phase II cultivation of Haematococcus cells (B above), each cultivation cycle being about five to six days optimally, the following harvesting procedure was performed, based on the fact that Haematococcus cells (especially red cells), in particular, those of the *H. pluvialis* strain employed in accordance with the invention, readily sediment, once collected from the tubular photobioreactor. Thus, the red cell biomass from the tubular photobioreactor was collected into a standard large volume feel (e.g., an Imhoff funnel, see step (6), FIG. 2) and left to stand for a few hours (about 3–5 hours) to facilitate sedimentation of the red cells. It was found that approximately 30% of the total volume of biomass from the tubular bioreactor represented the red cell sediment, while the remaining about 70% of the total collected volume represented the tap water used in the Phase II cultivation. This tap water could thus be easily collected and used for a new tubular bioreactor inoculation and Phase II cultivation procedure (ie., the originally used tap water is almost completely recyclable), this being another advantage of the method of the invention.

The above sedimented and concentrated Haematococcus red cell culture was then collected from the funnel and subjected to centrifugation or vacuum filtration to further concentrate the red cells. Routinely, a biomass yield of about 40% solids (pellet of red cells) was obtained following the centrifugation step (see step (7), FIG. 2), or about 30% solids following vacuum filtration. Here, too, the approximately 60% of the total volume subjected to centrifugation; or approximately 70% of the total volume subjected to vacuum filtration, being the supernatant volume, could also be collected and used for another round of the Phase II cultivation procedure, this supernatant being primarily the original tap water used in the Phase II procedure.

The concentrated red cell pellet obtained from the above centrifugation step was then dried, preferably by lyophilization, although spray drying also proved to be effective. The resulting dried powder was homogenized, packed into a plastic bag pre-filled with nitrogen gas to remove oxygen (which causes pigment oxidation, ie. degradation of the astaxanthin) and then stored at −20° C. prior to processing to prepare the food additive for fish coloration.

The above harvesting procedure, in accordance with the invention, is particularly advantageous in that standard equipment is utilizable and both the equipment and their maintenance are generally inexpensive and do not require highly skilled personnel for this operation. Further, about 70% of the initial red cell culture volume obtained from the Phase II cultivation is recyclable for further Phase II cultivations, and added to this, a further 60% of the initially sedimented red cell biomass, as obtained from the subsequent centrifugation of the sedimented red cells, is also recyclable for further Phase II cultivations. Accordingly, even a cheap resource such as the tap water used in the Phase II cultivation, is almost fully recyclable in the process of the invention.

D. Processing of the Harvested and Concentrated Haematococcus Red Cells for Extraction of Astaxanthin The dry powder of Haematococcus cells stored at −20° C. (C. above) was ground under these cryogenic conditions. The apparatus of choice used was a standard impact mill (see step (8), FIG. 2). To prevent oxidation of the astaxanthin during the grinding procedure, a commercial antioxidant was used such as, for example, ethoxyquin, butylated hydroxyanisole, butylated hydroxytoluene (BHT), tocopherols, di-tert-butyl-paracresol and propyl gallate. The preferred ant-oxidant was found to be BHT, which also has a U.S.-FDA approval making it particularly acceptable, in cases like the present, where the final product is intended for use as a food-additive for fish which, themselves, are ultimately intended for human consumption. Usually, depending on the anti-oxidant used, the amount of anti-oxidant added in the grinding procedure will range from about 0.05 to 5% (w/w) of the amount of dry powder being ground.

Routinely, it was found that the above processing procedure only resulted in a loss of about 10% of the astaxanthin.

The ground powder contaning the anti-oxidant for preservation of the astaxanthin from oxidation, as obtained from the above procedure, may then be utilized directly or in admixture with other ingredients, for example, edible oils and the like, as an additive to fish meal for the sake of coloration, as mentioned herein above (see steps (9) and (10) of FIG. 2).

REFERENCES

Borowitzka, M. A. (1992) Algal biotechnology products and processes—matching science and economics. J. Appl. Phycol. 4: 267–279.

Boussiba, S., Fan, L., Vonshak, A. (1992) Enhancement and Determinaon of Astaxanthin Accumulation in Green Alga *Hazematococcus pluvialis*. Methods in Enzymology, 213, Carotenoids Part A, Lester Packer (ed.), Academic Press: 386–371.

Boussiba, S., Vonshak, A. (1991) Astaxanthin Accumulation in the Green Alga *Haematococcus pluvialis*. Plant Cell Physiology, 32: 1077–1082.

Johnson, E. A., An, G. H. (1991) Astaxanthin from Microbial Sources. Critical Reviews in Biotechnology, 11: 297–326.

Kobayashi, M., Kakizono, T., Nagai, S. (1991) Astaxanthin Production by a Green Alga, *Haematococcus pluvialis* Accompanied with Morphological Changes in Acetate Media. J. of Fermentation and Bioengineering, 71: 335–339.

Richmond, A., Boussiba, S., Vonshak, A., Kopel, R. (1993) A new tubular reactor for mass production of microalgae outdoors, J. Appl. Phycol. 5: 327–332. Schroeder, W. A., Johson, E. A. (1993) Antioxidant role of carotenoids in *Phaffia rhodozyma*. J. General Microbiology 139: 907–912.

Tredici, M. R., Carlozzi, P., Chini Zittelli, G., Materassi R. (1991) A vertical alveolar panel (VAP) for outdoor mass cultivation of microalgae and cyanobacteria. Bioresource Technology, 38: 153–159.

Yokoyama, A., Miki, W. (1995) Composition and presumed biosynthetic pathway of carotenoids in the astaxanthin-producing bacterium *Agrobacterium aurantiacum*. FEMS Letters 128: 139–144.

We claim:

1. A process for cultivating Haematococcus cells for the large scale production of astaxanthin-enriched Haematococcus cells comprising:

(a) cultivating said Haematococcus cells under conditions suitable for optimal vegetative growth of said cells, wherein said conditions comprise growing the cells under a light intensity in the range of about 30–140 $\mu$mol photons.m$^{-2}$S$^{-1}$ and at a temperature of between about 15–28° C.; and (b) collecting the cells grown according to (a) and cultivating them further under conditions suitable for optimal induction and accumulation of astaxanthin in said cells, wherein said conditions comprise inoculating said cells of (a) into a growth solution consisting essentially of tap water to which is added $CO_2$ as the carbon source for the cells, and growing said cells at a temperature of below 35° C.

2. A process according to claim 1, wherein said optimal vegetative growth conditions of (a) are by growing said cells in a photobioreactor to facilitate the controlled environmental conditions of said light intensity and temperature.

3. A process according to claim 2, wherein said photobioreactor is a vertical photobioreactor.

4. A process according to claim 2, wherein said photobioreactor is a tubular panel photobioreactor.

5. A process according to claim 1, wherein the growth conditions of (a) further comprise growing said cells in Modified BG-11 medium and agitation of the cells by a flow of a mixture of $CO_2$ in air through the culture.

6. A process according to claim 1, wherein the initial concentration of cells used for the cultivation in (a) is about $0.1–0.3 \times 10^6$ cells/ml.

7. A process according to claim 1, wherein the cultivating step (a) comprises the conditions of growing the cells under a light intensity in the range of about 70–90 $\mu$mol photons.m$^{-2}$.s$^{-1}$ and at a temperature of between about 22–25° C.

8. A process according to claim 1, wherein said optimal conditions for the induction and accumulation of astaxanthin in the cells of (b) are by growing said cells in a photobioreactor to facilitate the effective maintenance of the temperature at below 35° C.

9. A process according to claim 8, wherein said photobioreactor is a tubular bioreactor.

10. A process according to claim 8, wherein said cultivation of (b) is carried out outdoors and the light source for the cells is sunlight.

11. A process according to claims 8, wherein said cultivation of (b) is carried out under conditions of temperature control at below 32° C.

12. A process for the large-scale production of astaxanthin-enriched Haematococcus cells comprising cultivating Haematococcus cells according to claim 1 and further comprising the steps:

(c) harvesting the cells cultivated in (b) by collecting said cells, concentrating the collected cells, drying the concentrated cells and freezing the dried cells; and (d) processing the frozen dried cells of (c) by grinding them under cryogenic conditions in the presence of a suitable antioxidant to obtain an astaxanthin-enriched product.

13. A process according to claim 12, wherein the collection and concentration of said cells is by sedimentation followed by centrifugation or filtration under vacuum, and wherein the drying of the said cells is by lyophilization, or by spray drying.

14. A process according to claim 12, wherein the grinding of said dry cells is by way of an impact mill.

15. A process according to claim 12, wherein the antioxidant is selected from the group consisting of ethoxyquin, butylated hydrox yanisole, butylated hydroxytoluene (BHT), tocopherols, di-tert-butyl-paracresol and propyl gallate.

16. A process according to claim 1, wherein the Haematococcus cells are of the strain *Haematococcus pluvialis*.

17. A process according claim 12, wherein the astaxanthin-enriched cells are *Haematococcus pluvialis* cells.

* * * * *